(12) United States Patent
Nozato

(10) Patent No.: US 8,888,283 B2
(45) Date of Patent: Nov. 18, 2014

(54) ABERRATION CORRECTION METHOD AND ABERRATION CORRECTION APPARATUS

(71) Applicant: Canon Kabushiki Kaisha, Tokyo (JP)

(72) Inventor: Koji Nozato, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 1 day.

(21) Appl. No.: 13/755,331

(22) Filed: Jan. 31, 2013

(65) Prior Publication Data

US 2013/0201448 A1 Aug. 8, 2013

(30) Foreign Application Priority Data

Feb. 8, 2012 (JP) ................................ 2012-025026

(51) Int. Cl.
*A61B 3/10* (2006.01)
*A61B 3/00* (2006.01)

(52) U.S. Cl.
USPC .......................................... 351/205; 351/246

(58) Field of Classification Search
USPC ................................................ 351/200–246
See application file for complete search history.

(56) References Cited

U.S. PATENT DOCUMENTS

| 7,522,276 B2 * | 4/2009 | Tojo et al. ................... 356/237.5 |
| 8,204,300 B2 | 6/2012 | Sugita et al. |
| 8,384,908 B2 | 2/2013 | Sugita et al. |
| 8,430,509 B2 * | 4/2013 | Hirose .......................... 351/206 |
| 2011/0096337 A1 | 4/2011 | Hirose et al. |
| 2012/0019780 A1 | 1/2012 | Nozato |
| 2012/0154746 A1 | 6/2012 | Nozato |

FOREIGN PATENT DOCUMENTS

JP 2011-104332 A 6/2011

* cited by examiner

*Primary Examiner* — Mohammed Hasan
(74) *Attorney, Agent, or Firm* — Fitzpatrick, Cella, Harper & Scinto

(57) ABSTRACT

To increase the speed of aberration correction, provided is an aberration correction method, including: a step of selecting a first polarized component of reflected light obtained by irradiating an object to be inspected with measuring light; a step of measuring an aberration of the first polarized component; a step of correcting the aberration of the first polarized component by controlling a first aberration correction unit in accordance with a measured value of the aberration of the first polarized component; and a step of correcting, in a case where a value of the aberration corrected in the first aberration correcting step is smaller than a predetermined value, an aberration of a second polarized component of the reflected light, which is different from the first polarized component, by controlling a second aberration correction unit based on a control for the first aberration correction unit in the case.

17 Claims, 7 Drawing Sheets

ABERRATION CORRECTION METHOD AND ABERRATION CORRECTION APPARATUS

BACKGROUND OF THE INVENTION

1. Field of the Invention

The present invention relates to an aberration correction method and an aberration correction apparatus.

2. Description of the Related Art

In recent years, as an image photographing apparatus for ophthalmic application, a scanning laser ophthalmoscope (SLO) and an imaging apparatus employing interference of low coherent light have been developed. The SLO two-dimensionally irradiates a fundus with laser light and receives reflected light reflected on the fundus to create an image of the fundus. The imaging apparatus employing the interference of the low coherent light is called an optical coherence tomography (OCT), which is used, in particular, to obtain a tomographic image of the fundus or a vicinity of the fundus. A type of the OCT includes a time domain OCT (TD-OCT) and a spectral domain OCT (SD-OCT), and other various types of OCTs have been being developed.

In particular, in recent years, there has been a progress in achieving an even higher resolution owing to a development of a high numerical aperture (NA) of the irradiation laser in the above-mentioned image photographing apparatus for the ophthalmic application.

However, when taking an image of a fundus, the image is taken through optical textures of an eye, such as a cornea and a lens. Therefore, as the resolution is increased, the quality of the taken image has become influenced significantly by aberrations of the cornea and the lens.

In order to cope with this problem, researches on an adaptive optics (AO)-SLO and an AO-OCT have been being progressed, in which the aberration of an eye is measured and an AO function for correcting the aberration is incorporated in an optical system. In general, the AO-SLO and the AO-OCT measure a wave front of the eye by using a Shack-Hartmann wave front sensor system. The Shack-Hartmann wave front sensor system measures the wave front of the eye by irradiating the eye with measuring light and receiving reflected light reflected on the eye with a CCD camera through a microlens array. The AO-SLO and the AO-OCT can take a high resolution image by driving a variable shape mirror and a spatial phase modulator to correct the measured wave front and taking an image of the fundus through the variable shape mirror and the spatial phase modulator. An image photographing apparatus employing two spatial light modulators is disclosed in Japanese Patent Application Laid-Open No. 2011-104332.

In general, when the NA of the irradiation laser is increased to increase the resolution, the amount of the aberration due to the optical textures of the eye, such as the cornea and the lens, is increased and the profile of the aberration becomes complicated. Although the aberration can be corrected by the AO, in order to correct a large aberration or a complicated profile aberration, it is required to measure the aberration with a high resolution and to drive a wave front correction device with a high resolution. In order to measure the aberration with a high resolution and to drive the correction device with a high resolution, a large number of calculations are required, causing a problem of increasing the calculation time.

Although a spatial phase modulator employing liquid crystal can be used to correct the wave front with a high resolution, only a specific polarized component can be corrected due to the nature of the liquid crystal. Therefore, multiple spatial phase modulators are needed to support both polarized components.

In the spatial phase modulator, control values to be instructed may differ even when performing the same wave front correcting due to the modulation characteristic, an initial distortion state, and the like of each individual spatial phase modulator. Therefore, when multiple spatial phase modulators are used, the calculation load is further increased, resulting in a decrease of a feedback speed of the aberration correction.

Further, the wave front measured by the wave front sensor is slightly different depending on the polarization due to a modulation error in the spatial phase modulator and the like. Therefore, the measurement accuracy is degraded when both polarizations are measured at the same time, resulting in a problem that the time to converge the aberration correction feedback is increased or the convergence cannot be obtained up to a sufficiently low aberration.

In particular, improvement of a processing speed is very important because the aberration of the eye requires a high-speed repetition of the aberration correction due to a constant change of a state of tears or a state of visibility adjustment of the eye. The high-speed aberration correction is particularly important when using multiple spatial light modulators as disclosed in Japanese Patent Application Laid-Open No. 2011-104332.

SUMMARY OF THE INVENTION

In view of the above-mentioned problem, the present invention is to increase the speed of the aberration correction by calculating the correction amount with an appropriate method in accordance with a state of the aberration correction and to provide an aberration correction apparatus that realizes the high-speed aberration correction.

In order to solve the above-mentioned problem, according to an exemplary embodiment of the present invention, there is provided an aberration correction method, including:

a selecting step of selecting a first polarized component of reflected light obtained by irradiating an object to be inspected with measuring light;

a first aberration measuring step of measuring an aberration of the first polarized component;

a first aberration correcting step of correcting the aberration of the first polarized component by controlling a first aberration correction unit in accordance with a measured value of the aberration of the first polarized component; and a second aberration correcting step of correcting, in a case where a value of the aberration corrected in the first aberration correcting step is smaller than a predetermined value, an aberration of a second polarized component of the reflected light, which is different from the first polarized component, by controlling a second aberration correction unit based on a control for the first aberration correction unit in the case.

Further, in order to solve the above-mentioned problem, according to another exemplary embodiment of the present invention, there is provided an aberration correction apparatus, including:

a selection unit configured to select a first polarized component of reflected light obtained by irradiating an object to be inspected with measuring light;

an aberration measurement unit configured to measure an aberration of the first polarized component;

a first control unit configured to correct the aberration of the first polarized component by controlling a first aberration correction unit in accordance with a measured value of the aberration of the first polarized component; and a second control unit configured to correct, in a case where a value of the aberration of the first polarized component corrected by the aberration correction unit is smaller than a predetermined value, an aberration of a second polarized component of the reflected light, which is different from the first polarized component, by controlling a second aberration correction unit based on a control for the first aberration correction unit in the case.

According to the present invention, it is possible to increase the speed of the aberration correction by operating the correction devices in accordance with the state of the aberration correction.

Further features of the present invention will become apparent from the following description of exemplary embodiments with reference to the attached drawings.

DESCRIPTION OF THE EMBODIMENTS

The modes for carrying out the present invention are described with reference to the following embodiments. The present invention is not limited by the following structures according to the respective embodiments. Further, an image photographing apparatus according to the present invention can be applied to an object to be inspected such as an eye to be inspected, skin, and internal organs.

(First Embodiment)

As a first embodiment of the present invention, a structure of a fundus image photographing apparatus (aberration correction apparatus) to which the present invention is applied is described with reference to FIG. 1.

In this embodiment, for example, an object to be inspected, which is an object to be measured, is an eye, and an aberration generated at the eye is corrected by an adaptive optical system to take an image of a fundus.

Figure 1:
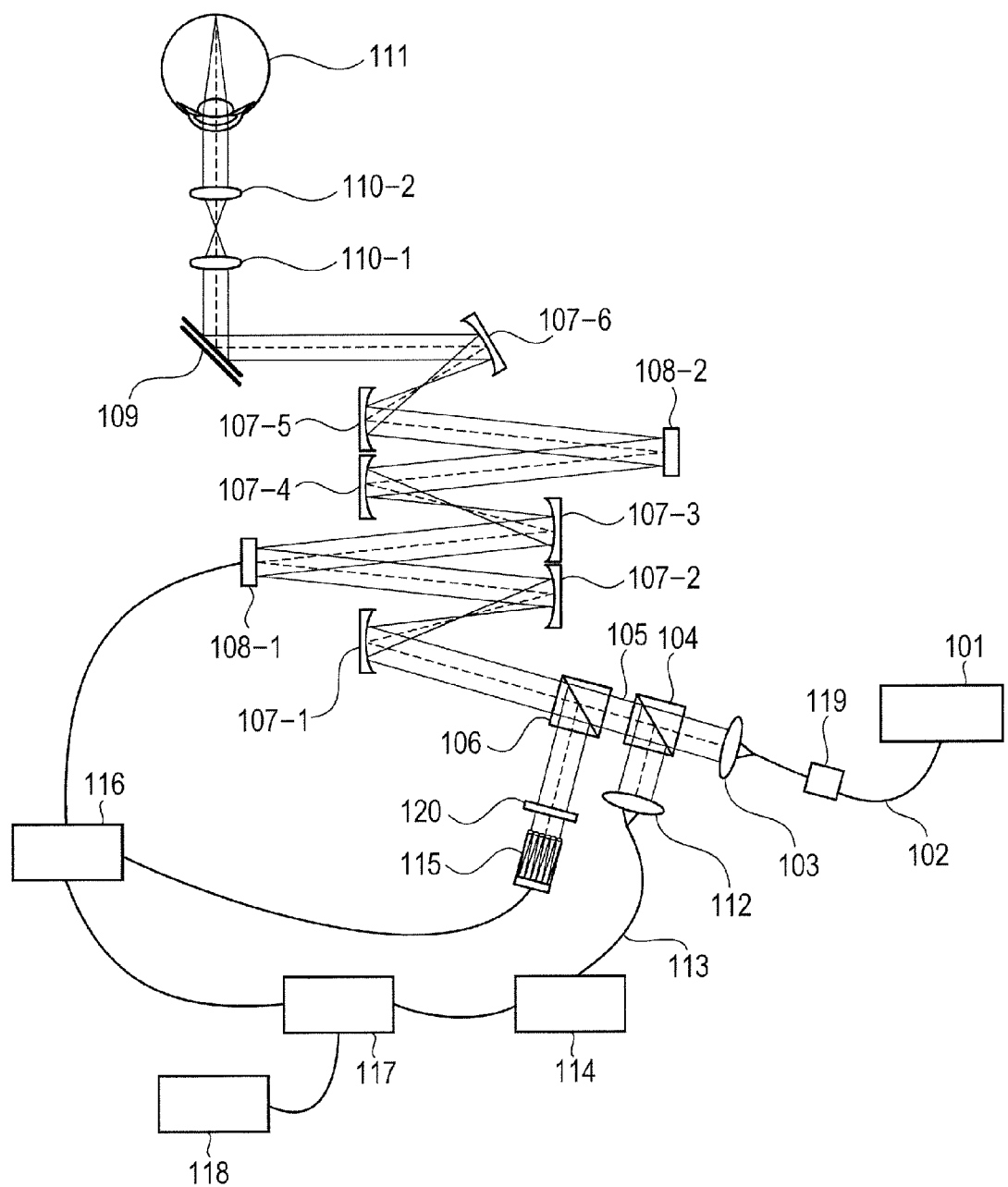
FIG. 1 is a schematic diagram illustrating a configuration example of a fundus image photographing apparatus (ophthalmic apparatus) using an SLO including an adaptive optical system according to a first embodiment of the present invention.

In FIG. 1, a light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare for a person to be inspected and maintain a resolution. In this embodiment, the SLD light source is used. In addition to such light source, for example, a laser light source may be used. In this embodiment, the light source is used in common for fundus image photographing and wave front measurement, but a structure may be employed in which respective light sources are provided separately and light beams therefrom are superimposed on each other on an optical path.

Light emitted from the light source 101 passes through a single-mode optical fiber 102, and is radiated as collimated light (measuring light 105) by a collimator 103. The polarization of the irradiated light is adjusted by a polarization adjusting member 119 provided on a path of the single-mode optical fiber 102. Another configuration may arrange an optical component for adjusting the polarization on an optical path after the collimator 103.

In this embodiment, the polarization adjusting member 119 is adjusted so that the polarized light exiting from the collimator 103 becomes a polarized component parallel to the drawing sheet of FIG. 1. This polarized light is referred to as first polarized light. Instead of the polarization adjusting member 119, a polarizing optical element such as a polarization plate may be arranged after the collimator 103.

The measuring light 105 radiated from the collimator 103 passes through a light division portion 104 including a beam splitter and then enters an adaptive optical system.

The adaptive optical system includes a light division portion 106, a wave front sensor 115, wave front correction devices 108-1 and 108-2, and reflective mirrors 107-1 to 107-6 for guiding the measuring light 105 to those components. The reflective mirrors 107-1 to 107-6 are provided so that at least a pupil of an eye 111, the wave front sensor 115, and the wave front correction devices 108-1 and 108-2 are in an optically conjugate relationship. In this embodiment, a beam splitter is used as the light division portion 106.

The measuring light 105 passing through the light division portion 106 is reflected on the reflective mirrors 107-1 and 107-2 to enter the wave front correction device 108-1. The measuring light 105 reflected on the wave front correction device 108-1 is further reflected on the reflective mirrors 107-3 and 107-4 to enter the wave front correction device 108-2, thereby traveling to the reflective mirror 107-5.

Figure 2:
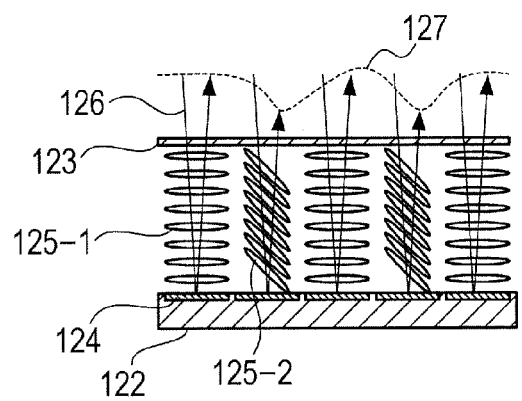
FIG. 2 is a schematic diagram illustrating an example of a wave front correction device according to the first embodiment of the present invention.

In this embodiment, a spatial phase modulator including a liquid crystal element is used as each of the wave front correction devices 108-1 and 108-2. FIG. 2 is a schematic diagram of a reflection-type liquid crystal light modulator. This modulator includes a base portion 122, a cover 123, and liquid crystal molecules 125 encapsulated in a space sandwiched by the base portion 122 and the cover 123. The base portion 122 includes multiple pixel electrodes 124. The cover 123 includes a transparent counter electrode (not shown). When no voltages are applied between the pixel electrodes and the counter electrode, the liquid crystal molecules are in such an orientation state as liquid crystal molecules 125-1. When voltages are applied, the orientation state is changed to such an orientation state as liquid crystal molecules 125-2, and hence a refractive index with respect to incident light changes. When a voltage is controlled for each of the pixel electrodes to change a refractive index of each pixel, spatial phase modulation may be realized. For example, when incident light 126 enters the modulator, light passing through the liquid crystal molecules 125-2 is delayed in phase from light passing through the liquid crystal molecules 125-1, to thereby form a wave front 127 as illustrated in FIG. 2. The reflection-type liquid crystal light modulator generally includes several ten thousand to several hundred thousand pixels.

The liquid crystal light modulator described above mainly modulates light of a specific polarized component. Therefore, in this embodiment, two wave front correction devices 108-1 and 108-2 are employed to modulate both polarized components, in which the modulating polarized components are substantially orthogonal to each other. The wave front correction device 108-1 modulates the first polarized component, and the wave front correction device 108-2 modulates a second polarized component that is orthogonal to the first polarized component.

In FIG. 1, the light reflected on the reflective mirrors 107-5 and 107-6 is one-dimensionally or two-dimensionally scanned by a scanning optical system 109. In this embodiment, two galvano-scanners are used as the scanning optical system 109 for main scanning (lateral direction of fundus) and sub scanning (longitudinal direction of fundus). In order to take an image at a higher speed, a resonance scanner may be used for the main scanning side of the scanning optical system 109. In order to bring the respective scanners included in the scanning optical system 109 into an optically conjugate relationship, optical elements such as a mirror and a lens may be used between the respective scanners depending on an apparatus structure.

The measuring light 105 scanned by the scanning optical system 109 is radiated to the eye 111 through eyepieces 110-1 and 110-2. The measuring light radiated to the eye 111 is reflected or scattered on the fundus. When the eyepieces 110-1 and 110-2 are adjusted in position, suitable irradiation may be performed in accordance with the diopter of the eye 111. Lenses are used for the eyepiece portion in this embodiment, but, for example, spherical mirrors may be used.

Reflected light which is produced by reflection or scattering on a retina of the eye 111 travels in the reverse direction on the same path as in the case of incidence. A part of the reflected light is reflected by the light division portion 106 to the wave front sensor 115 to be used for measuring a light beam wave front.

Figure 3A:
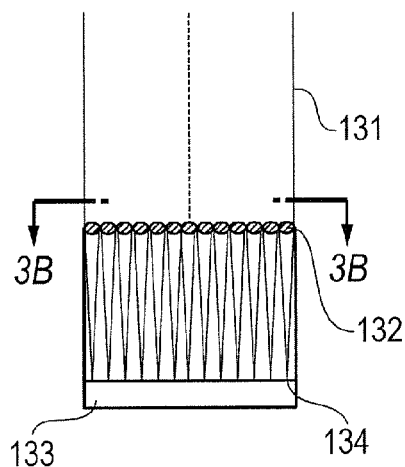
FIG. 3A is a schematic diagram illustrating a structure of a Shack-Hartmann sensor.
Figure 3B:
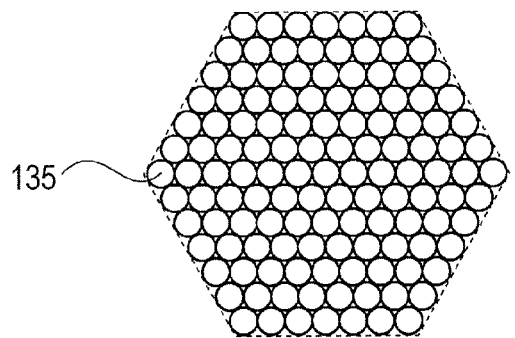
FIG. 3B is a schematic diagram illustrating a structure viewed from a position indicated by 3B-3B in FIG. 3A.
Figure 4:
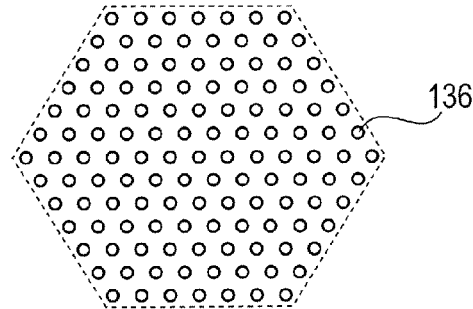
FIG. 4 is a schematic diagram illustrating a state in which a light beam for measuring a wave front is condensed on a CCD sensor.
Figure 5A:
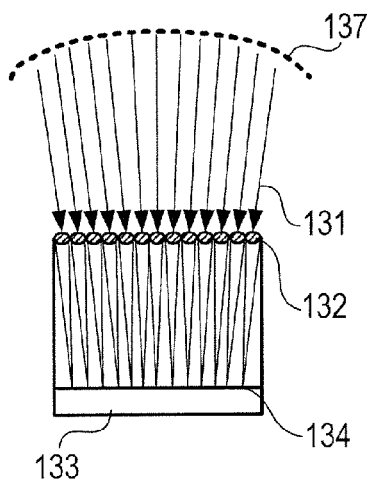
FIG. 5A is a schematic diagram illustrating a case where a wave front having a spherical aberration is measured.
Figure 5B:
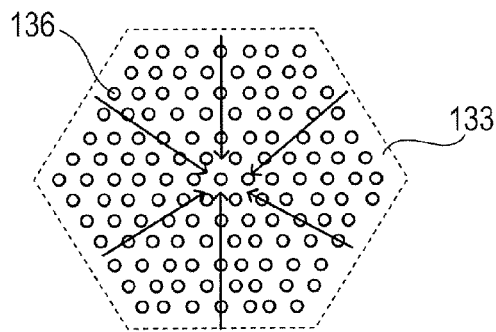
FIG. 5B is a schematic diagram illustrating a light condensing state on the CCD sensor in the case illustrated in FIG. 5A.

In this embodiment, a Shack-Hartmann sensor is used as the wave front sensor 115. FIG. 3A is a schematic view illustrating the Shack-Hartmann sensor. A light beam 131 for wave front measurement is condensed on a condensing surface 134 of a CCD sensor 133 through a micro-lens array 132. FIG. 3B illustrates a state as viewed from a position indicated by 3B-3B in FIG. 3A, and illustrates a state in which the micro-lens array 132 includes multiple micro-lenses 135. The light beam 131 is condensed on the CCD sensor 133 through the respective micro-lenses 135, and hence the light beam 131 is divided into spots equal in number to the micro-lenses 135 to form the spots. FIG. 4 illustrates a state in which the spots are formed on the CCD sensor 133. The light beam passing through the respective micro-lenses 135 is condensed to form spots 136. A wave front of the incident light beam is calculated based on the positions of the respective spots 136. For example, FIG. 5A is a schematic view illustrating a case where a wave front having a spherical aberration is measured. The light beam 131 is formed to have a wave front 137. The light beam 131 is condensed at positions in a direction of the local normal to the wave front by the micro-lens array 132. A focal state on the CCD sensor 133 in this case is illustrated in FIG. 5B. The light beam 131 has a spherical aberration, and hence the formed spots 136 are biased to the central portion. When the positions of the formed spots 136 are calculated, the wave front of the light beam 131 may be determined. In this embodiment, the Shack-Hartmann sensor is used as the wave front sensor. However, the present invention is not limited to this sensor. Another wave front measurement unit, for example, a curvature sensor may be employed or a method of obtaining the wave front by reverse calculation from the formed spot images may be employed.

A polarization plate 120 is arranged in front of the wave front sensor 115 so that only a specific polarized component among the reflected light from the eye enters the wave front sensor 115. In this embodiment, the reflected light is adjusted to the first polarized component by the polarization plate 120. The polarization plate 120 functions as a selection unit configured to select the first polarized component from the reflected light obtained by irradiating the fundus, which is an object to be inspected, with the measuring light 105 in the present invention. Further, the adjustment of the reflected light to the first polarized component corresponds to a selecting step in the present invention.

In FIG. 1, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a control unit 117 into an image as a fundus image and the fundus image is displayed on a display 118.

The wave front sensor 115 is connected to an adaptive optics control unit 116. The received wave front is transferred to the adaptive optics control unit 116. The wave front correction devices 108-1 and 108-2 are also connected to the adaptive optics control unit 116 and perform modulation instructed from the adaptive optics control unit 116. The adaptive optics control unit 116 calculates a modulation amount (correction amount) for correction to obtain wave front having no aberration based on the wave front obtained by a measuring result of the wave front sensor 115, and instructs the wave front correction devices 108-1 and 108-2 to perform the modulation according to the modulation amount. The wave front measurement and the instruction to the wave front correction device are repeated and feedback control is performed to always obtain a suitable wave front.

In a conventional apparatus, a wave front in which both polarized components are mixed is measured, and a modulation amount for correcting the wave front is calculated for each wave front correction device. However, each wave front correction device has an individual difference in the distortion component generated during manufacturing the wave front correction device and the driving voltage of the liquid crystal. Therefore, the control value to be instructed to the wave front correction device is required to be calculated as a different value for each wave front correction device even to form the same wave front. This calculation load is considerably heavy, resulting in a restriction on the feedback speed.

Figure 6:
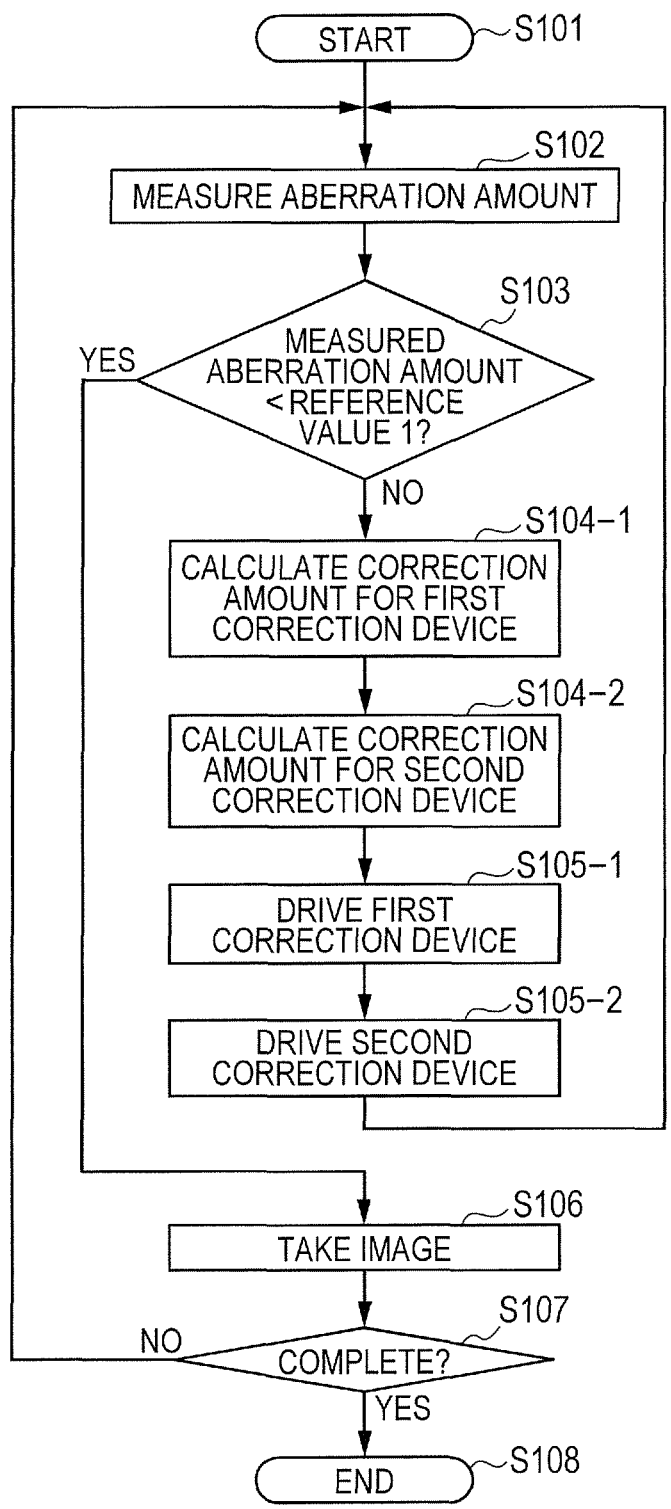
FIG. 6 is a flowchart of control steps in a fundus image photographing apparatus according to a conventional technology.

An example of the conventional control (aberration correction method) is described with reference to a flowchart illustrated in FIG. 6.

The control is started in Step S101 to execute a basic flow of the correction optics. In the basic flow of the adaptive optics, the aberration is measured by the wave front sensor 115 in Step S102, the correction amount is calculated by the adaptive optics control unit 116 in Step S104 based on the measured aberration, and the wave front correction device 108 is driven based on the control of the adaptive optics control unit 116 in Step S105, and these steps are repeated. Further, it goes without saying that the conventional measurement of the aberration by the wave front sensor 115 is performed in a state in which the polarization plate 120 is not present.

In practice, the wave front correction device 108 includes the first wave front correction device 108-1 and the second wave front correction device 108-2, and hence Step S104 for calculating the correction amount needs to be performed for each device. Therefore, Step 104-1 and Step 104-2 are performed. In addition, also regarding Step S105 for driving the device, Step 105-1 and Step 105-2 are needed to drive each device.

The aberration is measured and the aberration value or the aberration amount is obtained in Step S102. In Step S103, it is determined by the adaptive optics control unit 116 whether the obtained aberration amount falls below a reference value of the aberration amount set in advance. When it is determined that the obtained aberration amount exceeds the reference value of the aberration amount, the processes of Step S104 and subsequent steps are executed. On the other hand, when it is determined that the obtained aberration amount falls below the reference value of the aberration amount, the control proceeds to Step S106.

When the control proceeds to Step S106, an image is taken in Step S106, and in Step S107, it is determined whether taking the image is completed. When there is no request for completing taking the image, the processes of the adaptive optics from Step S102 to Step S105 are performed again, and the image is taken in Step S106. When there is a request for completing taking the image in Step S107, the control is ended in Step S108.

In this manner, Step S104 and Step S105 need to be performed in a redundant manner, which takes a considerable time.

Figure 7:
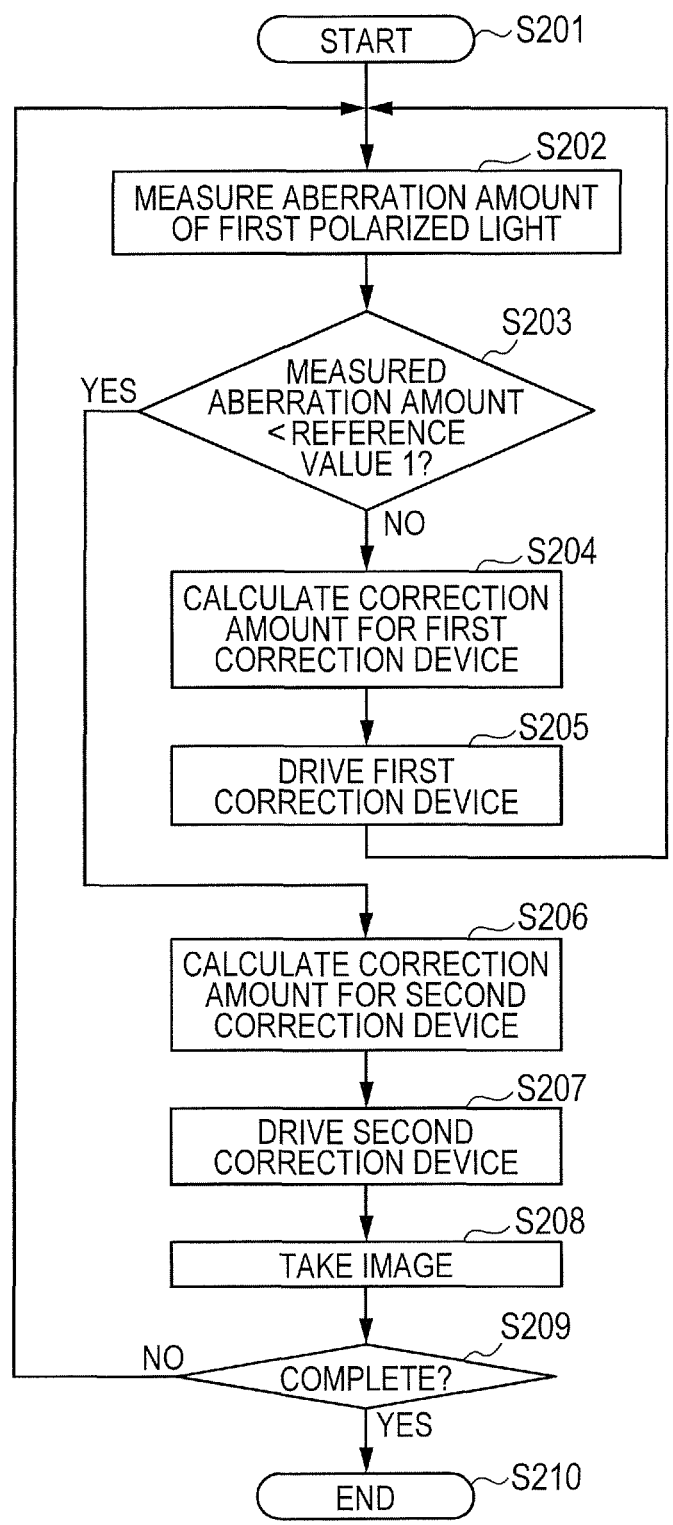
FIG. 7 is a flowchart of control steps in a fundus image photographing apparatus according to the first embodiment of the present invention.

A control (aberration correction method) according to this embodiment is described with reference to FIG. 7.

The control is started in Step S201 to execute a basic flow of the correction optics. In the basic flow of the adaptive optics, the aberration in the first polarized light is measured by the wave front sensor 115 in Step S202, the correction amount for the first wave front correction device 108-1 is calculated by the adaptive optics control unit 116 in Step S204 based on the measured aberration, the first wave front correction device 108-1 is driven based on the control of the adaptive optics control unit 116 in Step S205, and these steps are repeated. The measurement of the aberration in the first polarized light performed in Step S202 corresponds to a first aberration measuring step in the present invention. Further, the driving of the first wave front correction device 108-1 performed in Steps S204 and S205 corresponds to a first aberration correcting step in the present invention. While Steps S203 and S204 are repeated, the second wave front correction device 108-2 is driven by the adaptive optics control unit 116 in a predetermined driving state in which, for example, all pixels are in the orientation state 125-1 illustrated in FIG. 2. The wave front sensor 115 corresponds to an aberration measurement unit in the present invention, the first wave front correction device 108-1 corresponds to a first aberration correction unit in the present invention, and the second wave front correction device 108-2 that is described later corresponds to a second aberration correction unit in the present invention. The aberration correction unit is configured to correct the aberration of the reflected light obtained by irradiating the eye that is an object to be inspected with the measuring light. In addition, the adaptive optics control unit 116 corresponds to an example of a first control unit configured to control the first aberration correction unit in accordance with the measured value of the aberration of the first polarized component to correct the aberration of the first polarized component.

More specifically, in Step S202, the aberration of the first polarized component of the present invention is measured and the aberration amount is obtained as the measured value of the aberration. Although the aberration amount in the embodiments indicates a total amount of a disturbance of the wave front obtained from the aberration, it may be a total amount of a shift from a reference wave front (planar wave front). In Step S203, it is determined by the adaptive optics control unit 116 whether the obtained aberration amount falls below a reference value of the aberration amount set in advance, i.e., whether the measured value or the aberration amount is smaller than a predetermined value. In this manner, the adaptive optics control unit 116 functions as an aberration amount determination unit configured to determine whether the measured value of the aberration amount is smaller than the predetermined value in the above-mentioned processes. The reference value of the aberration amount may be a value unique to the apparatus or a value set by an operator. When it is determined that the obtained aberration amount exceeds the reference value of the aberration amount, the processes of Step S204 and subsequent steps are executed in a repeated manner. On the other hand, when it is determined that the obtained aberration amount falls below the reference value of the aberration amount, the control proceeds to Step S206.

When the control proceeds to Step S206, the correction amount for the second wave front correction device 108-2 is calculated with respect to the correction amount calculated last in Step S204 considering the individual difference between the first wave front correction device 108-1 and the second wave front correction device 108-2. Then, in Step S207, the second wave front correction device 108-2 is driven as a second aberration correcting step for correcting the second polarized component that is different from the first polarized component in the reflected light. That is, the control of the second wave front correction device 108-2 is executed in a mode in accordance with the control for the aberration correction by the first wave front correction device 108-1. More specifically, when the measured value of the aberration of the first polarized component obtained in the aberration correcting step is smaller than the predetermined value, the control of the second wave front correction device 108-2 is executed in a mode in accordance with the control of the first wave front correction device 108-1 performed in the previous aberration correcting step. In this case, the adaptive optics control unit 116 functions as an aberration correction control unit configured to cause the control modes of the first wave front correction device 108-1 and the second wave front correction device 108-2 to differ from each other. As described above, the wave front correction device employing the liquid crystal as in this embodiment has the individual difference in the distortion component during manufacturing the wave front correction device and the driving voltage of the liquid crystal. That is, even when the same voltage is simply applied to both the first wave front correction device 108-1 and the second wave front correction device 108-2, the corrected wave fronts may not be the same. In addition, even when the voltage applied to the second wave front correction device 108-2 is increased in the same manner as the first wave front correction device 108-1, the phase modulation amount with respect to the light is different in the second wave front correction device 108-2. Therefore, it is required to measure an initial applied voltage and the amount of fluctuation of the applied voltage in advance so that there is no difference in the wave front and the change amount of the wave front after correction, and to obtain a condition under which the respective correction devices are operated in the same mode. The process of calculating the correction amount considering the individual difference described above indicates an operation of measuring the operation condition in advance under which the respective correction devices are operated in the same manner as described above and obtaining the correction amount on which the operation condition is reflected when the correction operation is switched to the correction operation by the second wave front correction device 108-2 from the correction operation by the first wave front correction device 108-1. That is, by calculating different correction amounts for the first wave front correction device 108-1 and the second wave front correction device 108-2 considering the individual difference of the correction devices so that the wave fronts of the two polarized components become substantially the same as each other, as a consequence, different voltages are applied to the first wave front correction device 108-1 and the second wave front correction device 108-2. In addition, instead of obtaining the correction amount, the voltage to be applied to the second wave front correction device 108-2 may be obtained based on the voltage applied to the first wave front correction device 108-1 when the aberration amount is smaller than the predetermined value. The adaptive optics control unit 116 corresponds to an example of a second control unit configured to correct the aberration of the second polarized component that is different from the first polarized component by controlling, in a case where the value of the aberration of the first polarized component corrected by the first aberration correction unit is smaller than the predetermined value, the second aberration correction unit based on the control for the first aberration correction unit in the case.

After that, the image is taken in Step S208, and in Step S209, it is determined whether taking the image is completed. When there is no request for completing taking the image, the processes of the adaptive optics from Step S202 to Step S205 are performed again, and the control proceeds to Step S206. Although processes of taking the image and correcting the aberration are performed in a sequential manner in this embodiment, these processes can be performed in parallel. When there is a request for completing taking the image in Step S209, the control is ended in Step S210.

As described above, in the present invention, the control of the first wave front correction device 108-1 and the control of the second wave front correction device 108-2 are changed in the aberration correcting step based on the measured aberration amount that is a result of the aberration measuring step. By performing such processes, the calculation for controlling the second wave front correction device 108-2 is minimized (only one time at the last time) in the feedback of the aberration correction, and hence the calculation load is reduced and the speed of the feedback is increased, thereby enabling taking the image at high speed. This enables a load on a patient to be reduced.

(Second Embodiment)

Figure 8:
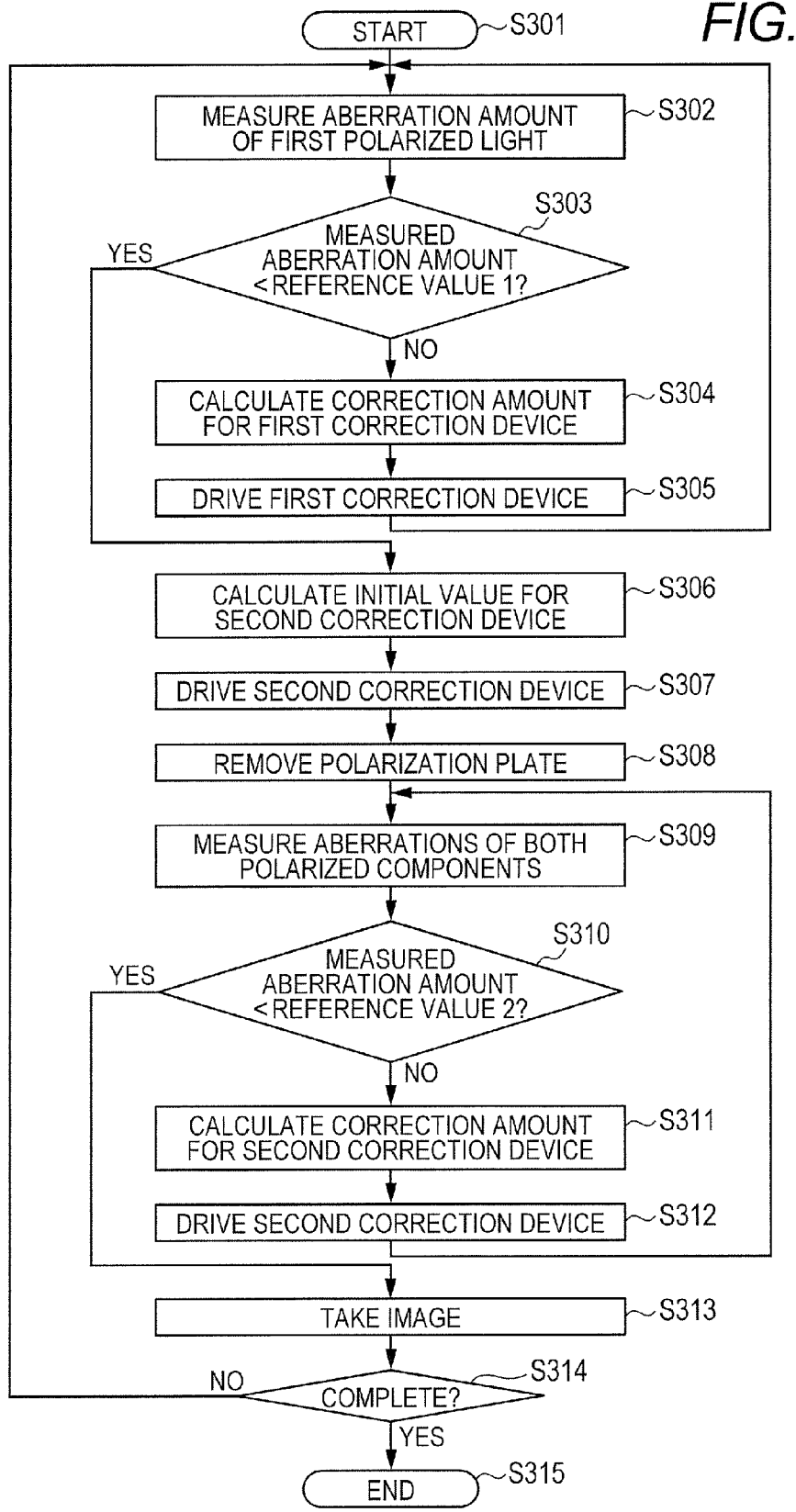
FIG. 8 is a flowchart of control steps in a fundus image photographing apparatus according to a second embodiment of the present invention.

As a second embodiment of the present invention, an example of a method of controlling a fundus image photographing apparatus to which the present invention is applied, which is different from that of the first embodiment, is described with reference to a flowchart illustrated in FIG. 8. In this embodiment, the basic configuration of the apparatus is the same as that of the first embodiment. However, this embodiment is different from the first embodiment in that a mechanism (not shown) for removing and inserting the polarization plate 120 is added to the configuration. The polarization plate 120 functions as a polarized component restriction unit in the present invention.

The control is started in Step S301. At this moment, the polarization plate 120 is arranged on the optical path of the apparatus.

The aberration in the first polarized light is measured by the wave front sensor 115 in Step S302, the correction amount for the first wave front correction device 108-1 is calculated by the adaptive optics control unit 116 in Step S304 based on the measured aberration, the first wave front correction device 108-1 is driven based on the control of the adaptive optics control unit 116 in Step S305, and these steps are repeated. The first wave front correction device 108-1 corrects the aberration of a polarized component that is different from the polarized component restricted by the polarization plate 120 as the polarized component restriction unit.

More specifically, the aberration is measured and the aberration amount is obtained in Step S302. In Step S303, it is determined by the adaptive optics control unit 116 whether the obtained aberration amount falls below a reference value of the aberration amount set in advance. The reference value of the aberration amount may be a value unique to the apparatus or a value set by an operator. When it is determined that the obtained aberration amount exceeds the reference value of the aberration amount, the processes of Step S304 and subsequent steps are executed. On the other hand, when it is determined that the obtained aberration amount falls below the reference value of the aberration amount, that is, the obtained aberration amount is smaller than a predetermined value, the control proceeds to Step S306. While Steps S302 to S305 are repeated, the second wave front correction device 108-2 is driven by the adaptive optics control unit 116 in a predetermined driving state in which, for example, all pixels are in the orientation state 125-1 illustrated in FIG. 2.

When the control proceeds to Step S306, the correction amount for the second wave front correction device 108-2 is calculated with respect to the correction amount calculated last in Step S304 considering the individual difference between the first wave front correction device 108-1 and the second wave front correction device 108-2. Then, in Step S307, the second wave front correction device 108-2 is driven.

In Step S308, the polarization plate 120 arranged right in front of the wave front sensor 115 is removed. With this arrangement, the wave front sensor 115 can measure the aberration of a state in which both polarized components exist in a mixed.

A feedback of the second aberration correction is then started. The feedback process includes a measurement of the aberration in Step S309, a comparison of the measured aberration amount with a reference value in Step S310, a calculation of the correction amount for the second wave front correction device 108-2 in Step S311, and a driving of the second wave front correction device 108-2 in Step S312. In this case, in the measurement of the aberration performed in Step S309, the polarized component of the aberration measured in the aberration measuring step is handled as the second polarized component to be corrected by the second wave front correction device 108-2. This feedback process is executed in a repeated manner. In the present invention, the aberration measuring step in the state in which both polarized components exist in a mixed manner is defined as a third aberration measuring step, and the following step of correcting the aberration is defined as a third aberration correcting step. In Step S310, when it is determined that the measured aberration amount is reduced to be smaller than the reference value, the control proceeds to Step S313 where the image is taken. When there is a request for completing taking the image in Step S314, the control is ended in Step S315. While Steps S309 to S312 are repeated, the first wave front correction device 108-1 is driven by the adaptive optics control unit 116 in a state right before proceeding to the Step S306.

By performing the above-mentioned processes, a complexity in driving multiple correction devices in a simultaneous manner is reduced, and the aberration can be corrected at high speed with high accuracy. That is, because the measurement of the aberration of the first polarized light and the measurement that does not depend on the polarized light are performed in a separate manner and the correction is performed based on the measurements, the speed of the feedback is increased, and the correction can be performed at even higher accuracy. In this embodiment, the polarized component corrected by the second aberration correction unit complies with the polarized component corrected by the first aberration correction unit. Therefore, it is preferred that the polarized component corrected by the first aberration correction unit be the same as the component of the measuring light to be used. From the same reason, it is more preferred that the polarized component corrected by the first aberration correction unit be the polarized component included in the reflected light at high proportion.

Further, in this embodiment, the polarization plate 120 is removed in Step S308. However, the polarization plate 120 may be rotated instead of being removed so that the operations from the measurement of the aberration to the correction of the aberration are repeated for the second polarized component that is different from the first polarized component. That is, after the aberration amount becomes smaller than the predetermined value in the operation of correcting the first polarized component, the polarization plate 120 is rotated to enable the measurement of the second polarized component, and the second aberration measuring step (Step S309) for measuring the aberration of the second polarized component and the second aberration correcting step (Step S312) for correcting this aberration may be repeated.

(Third Embodiment)

Figure 9:
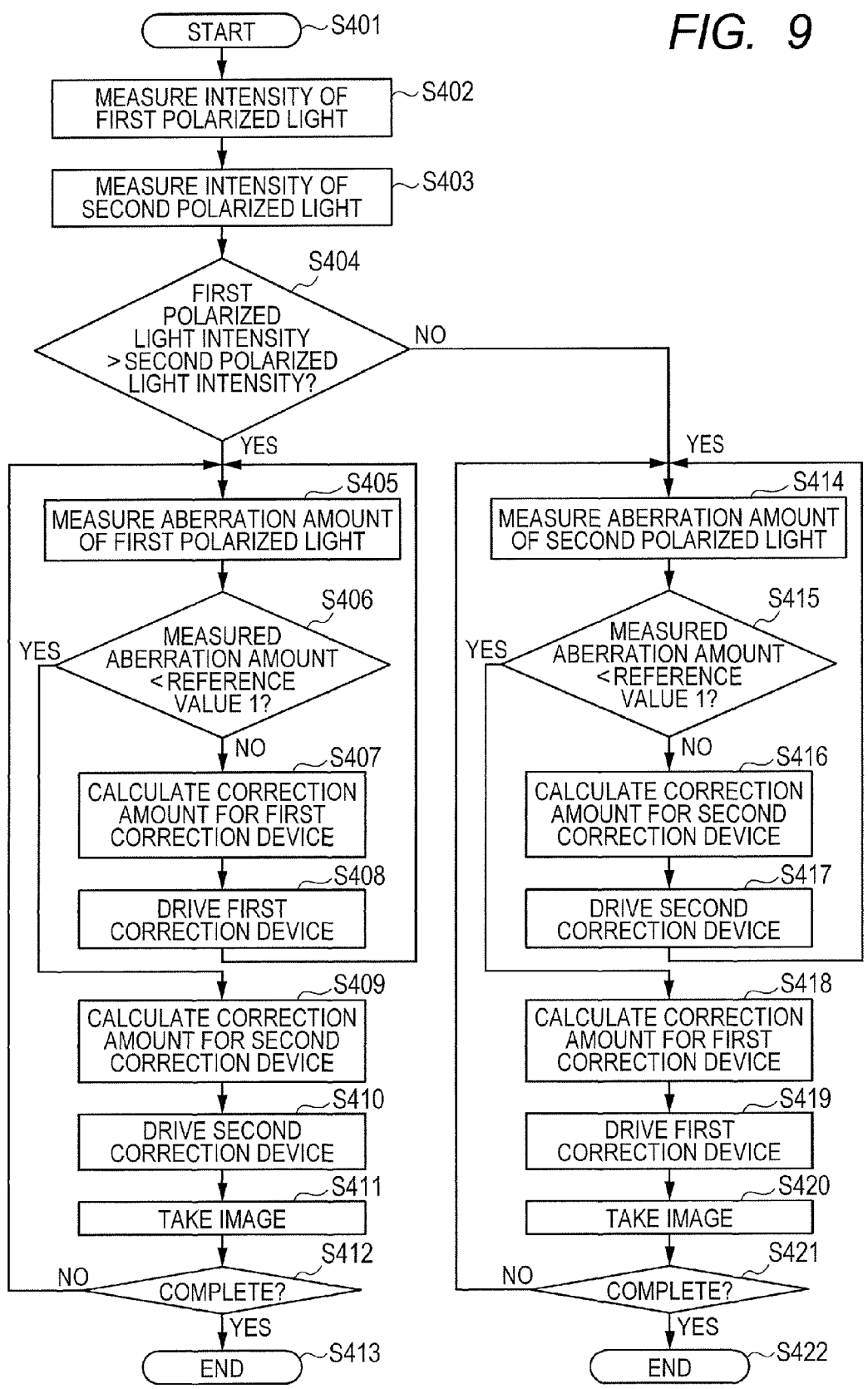
FIG. 9 is a flowchart of control steps in a fundus image photographing apparatus according to a third embodiment of the present invention.

As a third embodiment of the present invention, an example of a method of controlling a fundus image photographing apparatus to which the present invention is applied, which is different from that of the first embodiment, is described with reference to a flowchart illustrated in FIG. 9. In this embodiment, the basic configuration of the apparatus is the same as that of the first embodiment. However, in this embodiment, a mechanism (now shown) for rotating the polarization plate 120 by 90 degrees is added so that the polarized component that is mainly transmitted can be changed.

The control is started in Step S401. At this moment, the polarization plate 120 arranged on the optical path is set to transmit the first polarized component. In Step S402, the light intensity of the first polarized component is measured. The light intensity can be measured by the wave front sensor 115. Subsequently, in Step S403, the polarization plate 120 is rotated to mainly transmit the second polarized component, and the light intensity of the second polarized component is measured. The light intensity of the first polarized component and the light intensity of the second polarized component are then compared with each other in Step S404.

When the light intensity of the first polarized component is stronger than the light intensity of the second polarized component, the control proceeds to Step S405, and when the light intensity of the second polarized component is stronger than the light intensity of the first polarized component, the control proceeds to Step S414. After proceeding to Step S405 or S414, the same processes as those of the first embodiment are executed.

When the control proceeds to Step S405, in Step S405, the aberration in the first polarized light is measured by the wave front sensor 115, the correction amount for the first wave front correction device 108-1 is calculated by the adaptive optics control unit 116 in Step S407 based on the measured aberration, the first wave front correction device 108-1 is driven based on the control of the adaptive optics control unit 116 in Step S408, and these steps are repeated.

In Step S405, the aberration is measured and the aberration amount is obtained. In Step S406, it is determined by the adaptive optics control unit 116 whether the obtained aberration amount falls below a reference value of the aberration amount set in advance. The reference value of the aberration amount may be a value unique to the apparatus or a value set by an operator. When it is determined that the obtained aberration amount exceeds the reference value of the aberration amount, the processes of Step S407 and subsequent steps are executed. On the other hand, when it is determined that the obtained aberration amount falls below the reference value of the aberration amount, the control proceeds to Step S409. While Steps S405 to S408 are repeated, the second wave front correction device 108-2 is driven by the adaptive optics control unit 116 in a predetermined driving state in which, for example, all pixels are in the orientation state 125-1 illustrated in FIG. 2.

When the control proceeds to Step S409, the correction amount for the second wave front correction device 108-2 is calculated with respect to the correction amount calculated last in Step S407 considering the individual difference between the first wave front correction device 108-1 and the second wave front correction device 108-2. Then, in Step S410, the second wave front correction device 108-2 is driven. In Step S409, the aberration of the polarized component that is different from the polarized component corrected by the first wave front correction device 108-1 is corrected by the second wave front correction device 108-2.

After that, the image is taken in Step S411, and it is determined whether taking the image is completed in Step S412. When there is no request for completing taking the image, the processes of the adaptive optics from Step S405 to Step S408 are performed again, and the control proceeds to Step S409. Although processes of taking the image and correcting the aberration are performed in a sequential manner in this embodiment, these processes can be performed in parallel. When there is a request for completing taking the image in Step S412, the control is ended in Step S413.

When the control proceeds to Step S414, in Step S414, the aberration in the second polarized light is measured by the wave front sensor 115, the correction amount for the second wave front correction device 108-2 is calculated by the adaptive optics control unit 116 in Step S416 based on the measured aberration, the second wave front correction device 108-2 is driven based on the control of the adaptive optics control unit 116 in Step S417, and these steps are repeated.

In Step S414, the aberration is measured and the aberration amount is obtained. In Step S415, it is determined by the adaptive optics control unit 116 whether the obtained aberration amount falls below a reference value of the aberration amount set in advance. The reference value of the aberration amount may be a value unique to the apparatus or a value set by an operator. When it is determined that the obtained aberration amount exceeds the reference value of the aberration amount, the processes of Step S416 and subsequent steps are executed. On the other hand, when it is determined that the obtained aberration amount falls below the reference value of the aberration amount, the control proceeds to Step S418. While repeating Steps S414 to S417, the first wave front correction device 108-1 is driven by the adaptive optics control unit 116 in a predetermined driving state in which, for example, all pixels are in the orientation state 125-1 illustrated in FIG. 2.

When the control proceeds to Step S418, the correction amount for the first wave front correction device 108-1 is calculated with respect to the correction amount calculated last in Step S416 considering the individual difference between the first wave front correction device 108-1 and the second wave front correction device 108-2. Then, in Step S419, the first wave front correction device 108-1 is driven.

After that, the image is taken in Step S420, and it is determined whether taking the image is completed in Step S421. When there is no request for completing taking the image, the processes of the adaptive optics from Step S414 to Step S417 are performed again, and the control proceeds to Step S418. Although processes of taking the image and correcting the aberration are performed in a sequential manner in this embodiment, these processes can be performed in parallel. When there is a request for completing taking the image in Step S421, the control is ended in Step S422.

Further, as in the second embodiment, after the correction of the aberration by the first wave front correction device or the second wave front correction device is completed, a feedback of the aberration correction may be performed by using the other wave front correction device.

By performing the above-mentioned processes, the aberration of the polarized component that dominates the measuring light reflected on the eye can be corrected with priority in the feedback of the aberration correction. As a result, the calculation load can be reduced and the speed of the feedback can be increased while maintaining the accuracy, thereby enabling taking the image at high speed.

(Other Embodiments)

Further, the present invention is also realized by executing the following process. Specifically, in this process, software (program) for realizing the functions of the above-mentioned embodiments is supplied to a system or an apparatus via a network or various kinds of storage medium, and a computer (CPU, MPU, or the like) of the system or the apparatus reads out and executes the program.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2012-025026, filed on Feb. 8, 2012, which is hereby incorporated by reference herein in its entirety.

What is claimed is:

1. An aberration correction method, comprising:
a first aberration measuring step of measuring an aberration of a first polarized component of reflected light obtained by irradiating an object to be inspected with measuring light;
a first aberration correcting step of correcting the aberration of the first polarized component by controlling a first aberration correction unit in accordance with a measured value of the aberration of the first polarized component, wherein the aberration of the first polarized component is corrected by the controlled first aberration correction unit; and
a second aberration correcting step of correcting, in a case where a value of the aberration corrected in the first aberration correcting step is smaller than a predetermined value, an aberration of a second polarized component of the reflected light, which is different from the first polarized component, by controlling a second aberration correction unit based on a control for the first aberration correction unit in the case where the value of the aberration corrected in the first aberration correcting step is smaller than the predetermined value, wherein the aberration of the second polarized component is corrected by the controlled second aberration correction unit,
wherein the second aberration correction unit is different from the first aberration correction unit.

2. An aberration correction method according to claim 1, wherein:
the first aberration correcting step is performed when the measured value of the aberration of the first polarized component is equal to or larger than the predetermined value; and
the second aberration correcting step is performed when the measured value of the aberration of the first polarized component is smaller than the predetermined value.

3. An aberration correction method according to claim 1, wherein:
the first aberration measuring step and the first aberration correcting step are performed in a repeated manner; and
the second aberration correcting step is performed when the measured value of the aberration of the first polarized component obtained in the first aberration measuring step is smaller than the predetermined value.

4. An aberration correction method according to claim 1, further comprising a second aberration measuring step of measuring the aberration of the second polarized component of the reflected light obtained by irradiating the object to be inspected with the measuring light,
wherein the second aberration measuring step and the second aberration correcting step are performed in a repeated manner when the measured value of the aberration of the first polarized component obtained in the first aberration measuring step is smaller than the predetermined value.

5. An aberration correction method according to claim 1, further comprising:
a third aberration measuring step of measuring an aberration of the reflected light including the first polarized component and the second polarized component; and
a third aberration correcting step of correcting the aberration of the second polarized component in accordance with a measured value obtained in the third aberration measuring step,
wherein the third aberration measuring step and the third aberration correcting step are performed in a repeated manner after the second aberration correcting step is performed.

6. An aberration correction method according to claim 1, wherein the first polarized component includes a component of the same direction as a polarization direction of the measuring light.

7. An aberration correction method according to claim 1, wherein the first polarized component includes a polarized component having a highest proportion among multiple polarized components included in the reflected light.

8. A storage medium, which stores a program for causing a computer capable of reading the storage medium to execute the aberration correction method according to claim 1.

9. An aberration correction method according to claim 1, further comprising a selecting step of selecting the first polarized component of the reflected light obtained by irradiating the object to be inspected with the measuring light.

10. An aberration correction apparatus, comprising:
- an aberration measurement unit configured to measure an aberration of a first polarized component of reflected light obtained by irradiating an object to be inspected with measuring light;
- a first control unit configured to correct the aberration of the first polarized component by controlling a first aberration correction unit in accordance with a measured value of the aberration of the first polarized component; and
- a second control unit configured to correct, in a case where a value of the aberration of the first polarized component corrected by the first aberration correction unit is smaller than a predetermined value, an aberration of a second polarized component of the reflected light, which is different from the first polarized component, by controlling a second aberration correction unit based on a control for the first aberration correction unit in the case where the value of the aberration of the first polarized component corrected by the first aberration correction unit is smaller than the predetermined value,
- wherein the second aberration correction unit is different from the first aberration correction unit.

11. An aberration correction apparatus according to claim 10, wherein:
- the first control unit corrects the aberration of the first polarized component when the measured value of the aberration of the first polarized component is equal to or larger than the predetermined value; and
- the second control unit corrects the aberration of the second polarized component when the measured value of the aberration of the first polarized component is smaller than the predetermined value.

12. An aberration correction apparatus according to claim 10, wherein:
- the measuring of the aberration measurement unit and the correcting of the first aberration correction unit are performed in a repeated manner; and
- the second control unit corrects the aberration of the second polarized component when the measured value of the aberration of the first polarized component obtained in the first aberration measuring step is smaller than the predetermined value.

13. An aberration correction apparatus according to claim 10, further comprising a second aberration measurement unit configured to measure the aberration of the second polarized component of the reflected light obtained by irradiating the object to be inspected with the measuring light,
- wherein the measuring of the second aberration measurement unit and the correcting of the second aberration correction unit are performed in a repeated manner when the measured value of the aberration of the first polarized component is smaller than the predetermined value.

14. An aberration correction apparatus according to claim 10, further comprising:
- a third aberration measurement unit configured to measure an aberration of the reflected light including the first polarized component and the second polarized component; and
- a third control unit configured to correct the aberration of the second polarized component in accordance with a measured value obtained by the third aberration measurement unit,
- wherein the measuring of the third aberration measurement unit and the correcting executed by the third control unit are performed in a repeated manner after the correction of the second aberration correction unit is performed.

15. An aberration correction apparatus according to claim 10, wherein the first polarized component includes a component of the same direction as a polarization direction of the measuring light.

16. An aberration correction apparatus according to claim 10, wherein the first polarized component includes a polarized component having a highest proportion among multiple polarized components included in the reflected light.

17. An aberration correction apparatus according to claim 10, further comprising a selection unit configured to select the first polarized component of reflected light obtained by irradiating the object to be inspected with measuring light.

* * * * *